United States Patent
Baur et al.

(10) Patent No.: US 10,407,616 B2
(45) Date of Patent: Sep. 10, 2019

(54) SURFACTANT CONCENTRATES FOR PROMOTING SOIL HUMIDIFICATION AND PLANT GROWTH

(71) Applicant: Clariant International Ltd., Muttenz (CH)

(72) Inventors: Peter Baur, Schondorf (DE); Peter Klug, Grossostheim (DE)

(73) Assignee: Clariant International Ltd, Muttenz (CH)

( * ) Notice: Subject to any disclaimer, the term of this patent is extended or adjusted under 35 U.S.C. 154(b) by 50 days.

(21) Appl. No.: 15/307,205

(22) PCT Filed: Apr. 29, 2015

(86) PCT No.: PCT/EP2015/000871
§ 371 (c)(1),
(2) Date: Oct. 27, 2016

(87) PCT Pub. No.: WO2015/165586
PCT Pub. Date: Nov. 5, 2015

(65) Prior Publication Data
US 2017/0044434 A1 Feb. 16, 2017

(30) Foreign Application Priority Data

Apr. 30, 2014 (DE) .................. 10 2014 208 242

(51) Int. Cl.
| | |
|---|---|
| C05F 11/00 | (2006.01) |
| C09K 17/14 | (2006.01) |
| C09K 17/32 | (2006.01) |
| C05G 3/04 | (2006.01) |
| A01N 37/20 | (2006.01) |

(52) U.S. Cl.
CPC .............. *C09K 17/14* (2013.01); *A01N 37/20* (2013.01); *C05F 11/00* (2013.01); *C05G 3/04* (2013.01); *C09K 17/32* (2013.01)

(58) Field of Classification Search
CPC ........ C09K 17/14; C09K 17/32; A01N 37/20; A01N 25/30; A01N 57/12; A01N 39/04; A01N 57/20; A01N 43/66; A01N 37/38; A01N 43/54; A01N 41/12; A01N 41/10; A01N 37/40; C05G 3/04; C05F 11/00
See application file for complete search history.

(56) References Cited

U.S. PATENT DOCUMENTS

| | | | |
|---|---|---|---|
| 5,009,814 A | 4/1991 | Kelkenberg et al. | |
| 5,559,078 A * | 9/1996 | Garst .................. | A01N 25/30 424/405 |
| 6,350,788 B1 | 2/2002 | Herold et al. | |
| 6,455,001 B1 | 9/2002 | Knappe et al. | |
| 2005/0037926 A1 | 2/2005 | Zerrer et al. | |
| 2006/0166826 A1 | 7/2006 | Zerrer et al. | |
| 2015/0164755 A1 | 6/2015 | Klug et al. | |
| 2015/0320037 A1 | 11/2015 | Wacker et al. | |

FOREIGN PATENT DOCUMENTS

| | | |
|---|---|---|
| DE | 19701127 | 7/1998 |
| EP | 0285768 | 10/1988 |
| EP | 0550637 | 4/1995 |
| EP | 0995994 | 4/2000 |
| EP | 1379129 | 4/2004 |
| WO | WO 92/06073 | 4/1992 |
| WO | WO 96/16540 | 6/1996 |
| WO | WO 01/37658 | 5/2001 |
| WO | WO 02/089575 | 11/2002 |
| WO | WO 03/000055 | 1/2003 |
| WO | WO 2010/138661 | 12/2010 |
| WO | WO 2013/178670 | 12/2013 |
| WO | WO 2014/067663 | 5/2014 |

OTHER PUBLICATIONS

Mohammadi, R., et al., "Effect of Surfactants on Wetting of Super-Hydrophobic Surfaces", Langmuir, vol. 20, No. 22, Feb. 10, 2004 (Feb. 10, 2004), pp. 9657-9662, XP055098502, ISSN: 0743-7463, DOI: 10.1021/la049268k.
Walter, A., et al.: "Solubility properties of the alkylmethylglucamide surfactants", Biochimica and Biophysica ACTA, vol. 1029, No. 1, Nov. 2, 1990 (Nov. 2, 1990), pp. 67-74, XP023354648, ISSN: 0005-2736, DOI: 10.1016/0005-2736(90)90437-S.
English abstract for WO 01/37658, May 31, 2001.
International Search Report for PCT/EP2015/000871 dated Jul. 15, 2015.

* cited by examiner

*Primary Examiner* — Jennifer A Smith
(74) *Attorney, Agent, or Firm* — Tod A. Waldrop

(57) ABSTRACT

An aqueous composition which contains (a) one or more alkyl glucamides of the formula (I), wherein R1 represents a linear or branched alkyl group having 5 to 9 carbon atoms, R2 represents an alkyl group having 1 to 3 carbon atoms, and (b) water, is suitable for improving soil humidification.

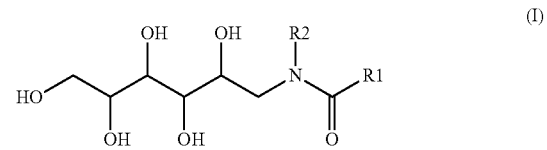

(I)

11 Claims, No Drawings

SURFACTANT CONCENTRATES FOR PROMOTING SOIL HUMIDIFICATION AND PLANT GROWTH

The invention relates to the use of glucamide-containing surfactant concentrates for improving soil humidification and plant growth, and to corresponding agents and methods.

It is known that the seemingly simple measure of watering areas of soil that are covered in particular with thick plant growth can present considerable difficulties. A typical example here is areas of grass that are subject to regular care that are worn in patches as a result of inspection and/or traversing. Thus, for example, when caring for golf courses or other comparable sports areas and playfields, despite regular watering, relatively small but also relatively large areas of the lawn can dry out. When attempting to humidify these areas, the water does not penetrate deeply enough into the soil and in particular not into the root area of the grasses.

So-called thatch is partly responsible for this, diverting the sprinkling water from the root area even above the soil surface, meaning that the corresponding plant areas become malnourished, shallow-rooted and diseased as a result of overdrying. The uniform distribution of the water upon reaching the soil surface can also present difficulties. Homogeneous spreading of the applied water, particularly in the region of the respective plant root zone, often does not take place. Rather, the applied water soaks, in spatially circumscribed streams, into deeper soil layers meaning that the damage stated above arises here too. Additional difficulties can arise in the presence of soil compression, which cannot be avoided particularly in the traversed and/or trodden areas.

The described problems relate not only to the process of watering. Corresponding difficulties also apply for the introduction of nutrients and/or protection substances in as uniform a distribution as possible in the area of the plant roots.

It is known to reduce the discussed problems by adding auxiliaries with a wetting agent character to the water used for the sprinkling and/or to the aqueous useful-material preparations; these reduce the surface tension of the water in a known manner and, in so doing, ensure better spreading of the aqueous phase over the entire soil area and thus in particular also in the area of plant rooting. In caring for sports fields, golf courses, but also in the field of protection of other green areas, practical use is made thereof.

DE-A 197 01 127 describes a low-foam wetting aid in the supply form of a highly concentrated, equally flowable and pourable aqueous concentrate based on surfactant for intensifying the penetration and spreading of water in the area of plant rooting during their watering which comprises alkyl (poly)glycoside compounds of the O/W type as ecologically compatible surfactant component. Besides this surfactant component, the aqueous concentrate comprises olefinically unsaturated fatty alcohols as defoamer/antifoam and finally additionally lower water-soluble alcohols as viscosity regulators.

WO 01/37658 proposes anionic cosurfactants for preventing foam formation in the above system.

Although good results have already been achieved with the known systems, there still remains much scope for improvements, especially as regards the homogenization, intensification and control of water entry into in particular soil areas with thick growth.

It has now been found that certain shorter-chain N-alkylglucamides are suitable in a particular manner as soil humidifiers and agents for promoting plant growth.

WO 96/16540 describes pesticide compositions which long-chain alkylamides which carry a polyhydroxycarbonyl substituent with at least three hydroxyl groups on the amide nitrogen. Emulsion concentrates, water-dispersible powders and granules of dodecyl-N-methylglucamide, dodecyltetraclecyl-N-methylglucamide and cetylstearyl-N-methylglucamide are described in the examples. Reference to a wetting effect of the described glucamides is not to be found in this document.

The invention therefore provides the use of an aqueous composition comprising
(a) one or more alkyl glucamides of the formula (I),

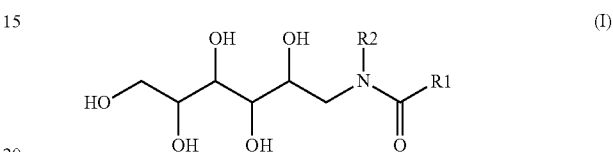

in which
R$^1$ is a linear or branched alkyl group having 5 to 9 carbon atoms,
R$^2$ is an alkyl group having 1 to 3 carbon atoms,
and
(b) water,
for improving soil humidification.

The invention furthermore provides the use of a composition according to the invention for promoting plant growth.

The invention likewise provides agents for improving soil humidification and/or plant growth, comprising a composition according to the invention.

The invention furthermore provides a method of improving soil humidification, where a composition according to the invention is applied to the soil.

The invention likewise provides a method of improving plant growth, where a composition according to the invention is applied to the soil on which the plants grow.

The compositions used according to the invention exhibit, besides high effectiveness as wetting agents for soils, excellent application properties and are ecologically advantageous since they are biodegradable, have low aquatic toxicity and are based on renewable raw materials.

According to the invention, the term "soil" means, according to a definition in the soil protection convention of the German Federal Government "the conversion product of mineral and organic substances with its own morphological organization that is permeated with water, air and living beings, has formed under the influence of environmental factors on the earth's surface and is further developing over the course of time and which is able to serve higher plants as habitat". The compositions used according to the invention act here particularly in the organic soil horizon (H, L, O horizon with organic layer). According to the invention, the term "crumb" refers to the upper soil layer in which plants grow.

According to the invention, "improving the soil humidification" means that a composition according to the invention comprising the component (a) has a wetting of the soil that is higher by at least 10%, preferably at least 20%, particularly preferably at least 50%, than a corresponding composition without the component (a). The wetting is measured here preferably in accordance with P. T. Bially, Esterified Alkyl Polyglucosides as Wetting Agents for Plant Growth Media, in P. Baur and M. Bonnet (Ed.) Proceedings of the 9th International Symposium on Adjuvants for Agrochemicals ISAA 2010, pp, 397-404, ISAA Society, Wageningon, the Netherlands 2010, ISBN 978-90-815702-1-3. Further parameters for quantifying the effects are the determination of the maximum and time-dependent water content of the soil as a function of the water potential and the rate at which the maximum water content is reached, which are described in relevant soil science books (e.g. Wilfried, Ehlers, "Wasser in Boden und Pflanze. Dynamik des Wasserhaushaltes als Grundlage von Pflanzenwachstum und Ertrag [Water in soil and plant. Dynamic of the water balance as the basis of plant growth and yield]" Ulmer 1996).

According to the invention, "improving the plant growth" means that as a result of watering with an agent according to the invention the area of plant growth on the watered area increases by at least 10%, preferably at least 20% or the biomass of the (above-ground) plant cover increases by at least 5%.

Depending on the soil composition and the supply of the plants with nutrients, it is also sometimes possible to generate qualitative features such as so-called greening effects or better turgescence by means of the agent according to the invention.

Compositions according to the invention comprise firstly concentrates in which the water content (b) is at most 60% by weight, secondly the watering liquids in which the fraction of concentrates according to the invention is not more than 5% by weight.

As component (a), the compositions according to the invention comprise one or more N-alkylglucamides of the formula (I),

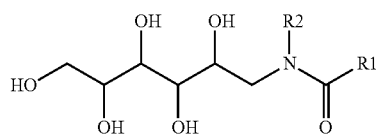

in which
R1 is a linear or branched alkyl group having 5 to 9 carbon atoms,
R2 is an alkyl group having 1 to 3 carbon atoms.

The preparation of the alkylglucamides of the formula (I) has already been sufficiently described and is known to the person skilled in the art (see e.g. EPA-A 0 550 637 and EP-A 0 285 768). It takes place for example by condensation of carboxylic acid esters with a secondary N-alkyglucamine which, for its part, can be prepared by reductive amination from a sugar such as the preferred D-glucose.

In the one or more alkylglucamides of the formula (I), the radical $R^1$ is preferably a linear or branched alkyl group having 7 to 9 carbon atoms. The radical $R^2$ is preferably a methyl group.

Particularly preferably, the compositions according to the invention comprise a mixture of octyl-N-methylglucamide ($R^1=C_7$-alkyl, $R^2$=methyl) and decyl-N-methylglucamide ($R^1=C_9$-alkyl, $R^2$=methyl). The fraction of octyl-N-methylglucamide in this mixture is 10 to 90% by weight, preferably 20 to 80% by weight and particularly preferably 30 to 70% by weight, based on the total amount of the alkylglucamides present in this mixture. The fraction of decyl-N-methylglucamide in this mixture is 10 to 90% by weight, preferably 20 to 80% by weight and particularly preferably 30 to 70% by weight, based on the total amount of the alkylglucamides present in this mixture. Preference is also given to nonyl-N-methylglucamide ($R^1=C_8$-alkyl, $R^2$=methyl, based on pelargonic acid).

The pentahydroxyhexyl radical in the alkylglucamides of the formula (I) has various chiral centers, meaning that two or more stereoisomers can exist in each case. Usually, the alkylglucamides of the formula (I) are prepared from naturally occurring sugars, such as D-glucose, although in principle it is also possible to use different natural or synthetic hexoses or different $C_6$ budding blocks, meaning that different stereoisomers of the formula (I) can result.

Preferably, concentrates according to the invention comprise 10 to 70% by weight, particularly preferably 20 to 60% by weight and especially preferably 40 to 55% by weight, of the one or more alkylglucamides of component (a).

As component (b), the compositions according to the invention comprise water. Suitable as water are, for example, desalinated water, ground water, seawater or tap water. Preferably, the water has a hardness of less than 15° German hardness.

The water content in concentrates according to the invention is preferably 20 to 50% by weight, particularly preferably 30 to 45% by weight, especially preferably 40 to 45% by weight.

Besides the components (a) and (b), the compositions according to the invention preferably comprise
c) one or more polyols, preferably from the group propylene glycol, glycerol, dipropylene glycol, and mixtures of propylene glycol and dipropylene glycol, in each case optionally in a mixture with polypropylene glycol and/or polyethylene glycol, in each case with up to ten repeat units, particularly preferably propylene glycol and/or glycerol.

The content of polyol in concentrates according to the invention is preferably 1 to 30% by weight, particularly preferably 2 to 10% by weight, especially preferably 2 to 5% by weight.

In a further preferred embodiment, as component (d), lower water-soluble monofunctional alcohols are used as viscosity regulators. Preference is given to corresponding compounds from the range $C_{1-4}$, with ethanol being attributed the most important role as viscosity regulator. The viscosity regulator is determined in its use amount by the other components according to type and amount and the amount of water present overall in the multisubstance mixture.

If a viscosity regulator is present in a concentrate according to the invention, then the amounts, preferably leased on ethanol, are in the range from 5 to 7% by weight as lower limit and 12 to 15% by weight as upper limit. Ethanol amounts in the range from about 10 to 15% by weight generally produce an adequate viscosity influence in the sense of a desired flowability and pourability of the concentrate even in the region of room temperature.

In a further preferred embodiment, the compositions according to the invention comprise one or more antifoams as component (e).

Preferably used antifoams are firstly antifoams based on silicone, preferably selected from the group of linear polydimethylsiloxanes, where the ratio of dynamic surface tension (DYOS in [mN/m]) at a concentration of 2.0 g/l and a surface age of 20 milliseconds (ms) in 20% strength by weight aqueous propylene glycol to the dynamic surface tension under identical conditions in 20% strength by weight aqueous dipropylene glycol is greater than 1.10 and the ratio of the dynamic surface tension at a concentration of 2.0 g/l and a surface age of 20 ms in 20% strength by weight aqueous propylene glycol to the dynamic surface tension at a concentration of 10.0 g/l and a surface age of 20 ms in tap water is greater than 1.10.

Such antifoams according to the invention can be ascertained from the known commercial products on the basis of the above definition by means of a few simple routine experiments. Suitable examples are the products sold under the names SAG® 1572 (Momentive), Silfoam® SE3060 (Wacker) and Break Thru® AF 9903 (Evonik).

The ratio according to the invention of dynamic surface tension of the antifoam at a concentration of 2.0 g/l and at 20 ms in 20% by weight propylene glycol to the dynamic surface tension under identical conditions in 20% by weight dipropylene glycol is greater than 1.10. The water used is preferably tap water with 15° German hardness. The dynamic surface tension is determined according to the invention in accordance with the bubble pressure method, for example using a tensiometer BP2100 from Krüss GmbH.

In a further preferred embodiment, the antifoam component (e) used is one or more olefinically unsaturated fatty alcohols from the range $C_{12-24}$, with corresponding fatty alcohols of natural origin being attributed particular importance here. Within this class, in turn those fatty alcohols or fatty alcohol mixtures with a high degree of olefinic double bonds are particularly preferred mixing components that are assigned to an at least predominant fraction to the range of $C_{16/18}$-fatty alcohols. As is known, the extent of the olefinic double bonds in the fatty alcohol molecule determines the solidification range of the particular valuable substance material. According to the invention, preference is given to corresponding fatty alcohols or fatty alcohol mixtures which have solidification ranges below 20 to 25° C. and in particular corresponding solidification values in the range less than or equal to 10 to 15° C.

The antifoam component based on fatty alcohols is present—if present—in the concentrates according to the invention preferably in amounts of from 3 to 25% by weight and particularly preferably in the range from about 5 to 20 10% by weight.

In a further embodiment, the antifoam (e) is anionic surfactants, in particular sulfosuccinic acid esters and salts thereof, as proposed in WO 01/37658.

In a further embodiment, the compositions according to the invention comprise, as component (f), one or more further surfactants different from the components (a) to (e), preferably the alkyl (poly)glycoside compounds described in DE-A 197 01127. Such compounds are produced during the reaction of fatty alcohols with glucose, oligoglucoses or else—in the case of simultaneous degradation of the chain length—with polyglycosides such as starch as reaction products of the general formula R—O-(G)x, in which R is a primary, preferably straight-chain and aliphatic hydrocarbon radical having in particular 8 to 18 carbon atoms, and G is a glycose unit having 5 or 6 carbon atoms, preferably glucose. The degree of oligomerization x, which indicates the distribution of monoglycosides and oligoglycosides, in the surfactant class under discussion here is usually a value between 1 and 10 and is, for example, in the range from about 1.2 to 4, preferably in the range from about 1.2 to 2. Reference may be made to the extensive expertise and literature relating to the preparation and properties of such compounds.

Preferred alkyl (poly)glycoside compounds comprise alkyl radicals based on largely saturated so-called precursor fatty alcohols, i.e. based on fatty alcohols having 8 to 14 and in particular 8 to 12 carbon atoms. Of particular suitability as further surfactants (f) are reaction products of $C_{8/10}$ fatty alcohols and glucose, oligoglucoses and/or polyglycoses. The so-called DP value (average degree of polymerization or degree of oligomerization x in the formula given above) is here too in the range from 1 to 10 and preferably in the range from 1 to 5, in particular in the range from about 1.2 to 4.

Furthermore, the compositions according to the invention can comprise ethylene oxide/propylene oxide block copolymers as component (f). Of suitability for this purpose are e.g. an ethylene oxide-propylene oxide block copolymer with an average molecular weight of 2800 g/mol, such as Genapol PF40 or 8000 g/mol such as Genapol PF80 or 6000 g/mol, such as Genapol® 10500 (Clariant) or Pluronic® 10500 (BASF).

In a further embodiment, the compositions according to the invention can comprise, as component (f), modified polyglycerol esters as are described e.g. in WO 03/000055. These are one or more copolymers, where the copolymers comprise one or more structural units derived from
a) glycerol,
b) at least one dicarboxylic acid and
c) at least one monocarboxylic acid according to formula (I)

$$R^1\text{—COOH} \tag{II}$$

where $R^1$ is $(C_5\text{-}C_{29})$-alkyl; $(C_7\text{-}C_{29})$-alkenyl; phenyl or naphthyl.

The fundamentally possible compositions of the copolymers, as well as preparation and embodiments of the copolymerization are described in WO 03/000055 and EP 1 379 129. A common feature of all of these is that the condensation reactions proceed between alcohols and/or carboxylic acids, i.e. the monomers are bonded together by ether bonds (in the case of the condensation of two alcohol functions of glycerol) or by ester bonds (in the case of the condensation of an alcohol function of glycerol with a carboxylic acid function of the mono- or dicarboxylic acid).

Corresponding copolymers are commercially available e.g. as Synergen® GL5 and Synergen® B01 from Clariant.

If the components (f) are present, the sum of the amounts used in the concentrate is usually 1 to 30, preferably 10 to 25, particularly preferably 15 to 20% by weight.

Optionally, the compositions according to the invention comprise further customary auxiliaries (g). Customary auxiliaries (g) are, for example, inert materials, such as adhesives, wetting agents, dispersants, emulsifiers, penetration substances, dyes, preservatives and antifreezes, fillers, carriers and dyes, evaporation preventers and agents that influence the pH (buffers, acids and bases such as citric acid, hydrochloric acid, sodium hydroxide solution) or which influence the viscosity (e.g. thickeners). Preferred auxiliaries (g) are antifreezes and evaporation preventers such as glycerol or ethylene glycol, e.g. in an amount of from 2 to 10% by weight and preservatives, e.g. Mergal K9N® (Riedel) or Cobate C®.

If the component (g) is present, the amounts used are usually 0.1 to 10, preferably 0.2 to 5, particularly preferably 0.3 to 3% by weight.

In general, the components (a) to (g) are present in the concentrates according to the invention in the following amounts:
a) 10 to 70% by weight of one or more N-alkylglucamides of the formula (I), as stated above,
b) 10 to 60% by weight of water,
c) 0 to 10% by weight of polyol,
d) 0 to 20% by weight, preferably 1 to 20, particularly preferably 2 to 10, of one or more viscosity regulators,
e) 0 to 10% by weight of one or more antifoams, f) 0 to 30% by weight, preferably 0 to 25% by weight, in particular 0 to 20% by weight of one or more further surfactants and g) 0 to 10% by weight, preferably 0 to 5% by weight, in particular 0 to 3% by weight, of one or more auxiliaries.

The weight ratio of the N-alkylglucamides a) to the polyol c is generally in the range from 10:1 to 4:1.

The weight ratio of the N-alkylglucamides a) to the viscosity regulators d) is generally in the range from 10:1 to 5:1.

The weight ratio of the N-alkylglucamides b) to the antifoam e) is generally in the range from 5:1 to 200:1.

The compositions according to the invention, in particular the concentrates, consist preferably of the components (a) to (h). Preferably, they comprise no agrochemical active ingredients and/or fertilizers.

In a further embodiment, the concentrates according to the invention comprise, as component (h) trace elements such as salts of iron, manganese or zinc.

Even upon adding very small amounts of, for example, 0.1% by weight—based on the total water used for the watering—the compositions according to the invention can trigger the desired effects of uniform humidification of the soil and preferably of the plants including in their entire root region with the aqueous phase. Preferred use amounts for the concentrates defined above in the water used for the watering are in the range from 0.1 to 5% by weight and in particular in the range from about 0.5 to 2% by weight—in each case based on the total aqueous phase.

The compositions according to the invention can also serve for the intensification of the entry of nutrients and/or protective substances such as herbicides, insecticides and/or fungicides for promoting and for improving plant growth. These additional active ingredients can be applied in a manner known per se in the form of aqueous solutions, emulsions and/or dispersions, where then, in the sense of the teaching according to the invention, compositions according to the invention are co-used.

The invention is explained in more detail by the example without thereby limiting it.

EXAMPLES

In the examples which follow, quantitative data refers to the weight, unless stated otherwise.

The glucamides (a) according to the invention used were:
GA1: 50% by weight of a mixture of 50 to 70% by weight C8-glucamide and 30 to 50% by weight of C10-glucamide, 5% by weight of propylene glycol and 45% by weight of water.
Concentrate 1
GA 1 is used as concentrate 1.
Concentrate 2
20% by weight glucamide GA1 (a)
3% by weight propylene glycol (c)
10% by weight Genapol® 10500, Clariant (EO/PO block polymer) (f)
10% by weight Synergen GL 5, Clariant (polyglycerol ester crosslinked with phthalic anhydride) (f)
57% by weight water (b)

Application Example 1

The testing of the concentrates in practical use is undertaken as follows:

A section of lawn with extensive dry patches was divided into two approximately equally sized segments with comparable damage patterns.

The areas here have the following dimension:
Experimental area A: 25 m×16.5 m=412.5 m² Experimental area B: 24 m×17.5 m=420 m².

Both areas are adequately artificially watered in the same manner during the entire experimental period according to the amount of natural rainfall. In this connection, area A is watered without further additions to the artificially applied water. In the case of area B, 250 ml of concentrate 1 are applied per 100 m² at the start of the experiment with the applied artificial sprinkling water. An analogous treatment was undertaken after three weeks and again after a further four weeks in the case of experimental area B. Assessment of the two areas after ten weeks gives the following picture:
Area A:
No change to the damage pattern; no change to the expanse of dry patches.
Area B:
Reduction in the expanse of dry patches by 70%. Extensive recovery of plant growth in the regenerated patch areas.

Application Example 2

The maximum water retention capacity is determined with samples of the soil type sandy loam according to USDA or "silty sand" according to LUFA standard soil 2.3 (http://www.lufa-speyer.de/images/stories/bodanalyse.pdf). This has a value of 37.3% (g/100 g) and is increased by the products according to the invention by at least 3% for an area dose of 1-2.5 g of concentrate per m², which is applied to the dry soil by means of large-drop spraying (injector nozzle) nozzle. The products have a contact time of at least one day and the effect lasts at least one month without eluviation by rain.

The invention claimed is:

1. A method for improving soil humidification, comprising the step of contacting the soil with at least one aqueous composition, wherein the aqueous composition comprises
   (a) at least one alkyl glucamide of the formula (I),

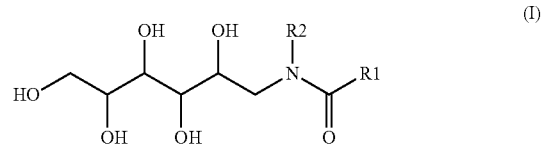

(I)

in which
R¹ is a linear or branched alkyl group having 5 to 9 carbon atoms,
R² is an alkyl group having 1 to 3 carbon atoms, and
(b) water,
with the proviso that the aqueous composition does not comprise an agrochemical active ingredient.

2. The method as claimed in claim 1, wherein R¹ is a linear or branched alkyl group having 7 to 9 carbon atoms and R² is a methyl group.

3. The method as claimed in claim 1, wherein the at least one alkyl glucamide of the formula (I) is a mixture of octyl-N-methylglucamide, R¹=C₇-alkyl, and decyl-N-methylglucamide, R¹=C₉-alkyl, where the fraction of octyl-N-methylglucamide is 10 to 90% by weight, and the fraction of decyl-N-methylglucamide is 10 to 90% by weight, based on the total amount of the alkylglucamides present in this mixture.

4. The method as claimed in claim 1, wherein the fraction of the at least one alkylglucamide of the formula (I) is a) 1 to 80% by weight, based on the total weight of the composition.

5. The method as claimed in claim 1, where the aqueous composition is a concentrate and comprises
   a) 10 to 70% by weight of the at least one N-alkylglucamide of the formula (I),
   b) 10 to 60% by weight of water,
   c) 0 to 10% by weight of polyol,
   d) 0 to 20% by weight, of one or more viscosity regulators,
   e) 0 to 10% by weight of one or more antifoams,
   f) 0 to 30% by weight, of one or more further surfactants and
   g) 0 to 10% by weight, of one or more auxiliaries.

6. The method as claimed in claim 1, where the aqueous composition, further comprises at least one surfactant, selected from the group consisting of alkyl (poly)glycoside compounds, ethylene oxide/propylene oxide block copolymers, modified polyglycerol esters, comprising one or more structural units derived from
   a) glycerol,
   b) at least one dicarboxylic acid and
   c) at least one monocarboxylic acid according to formula (II)

$$R^1\text{—COOH} \quad (II)$$

where $R^1$ is $(C_5\text{-}C_{29})$-alkyl, $(C_7\text{-}C_{29})$-alkenyl, phenyl or naphthyl,
and mixtures thereof.

7. The method as claimed in claim 1, wherein the at least one alkyl glucamide of the formula (I) is a mixture of octyl-N-methylglucamide, and decyl-N-methylglucamide, where the fraction of octyl-N-methylglucamide is 20 to 80% by weight and the fraction of decyl-N-methylglucamide is 20 to 80% by weight, based on the total amount of the alkylglucamides present in this mixture.

8. The method as claimed in claim 1, wherein the at least one alkyl glucamide of the formula (I) is a mixture of octyl-N-methylglucamide, and decyl-N-methylglucamide, where the fraction of octyl-N-methylglucamide is 30 to 70% by weight, and the fraction of decyl-N-methylglucamide is 30 to 70% by weight, based on the total amount of the alkylglucamides present in this mixture.

9. The method as claimed in claim 1, wherein the fraction of the at least one alkylglucamide of the formula (I) is a) 20 to 80% by weight, based on the total weight of the composition.

10. The method as claimed in claim 1, wherein the fraction of the at least one alkylglucamide of the formula (I) is a) 30 to 70% by weight, based on the total weight of the composition.

11. A method for promoting plant growth, comprising the step of applying at least one aqueous composition, wherein the aqueous composition comprises
    (a) at least one alkyl glucamide of the formula (I),

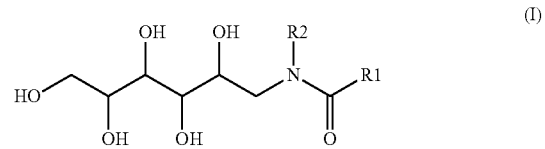

in which
$R^1$ is a linear or branched alkyl group having 5 to 9 carbon atoms,
$R^2$ is an alkyl group having 1 to 3 carbon atoms,
and
(b) water,
to a soil within which the plant is growing,
with the proviso that the aqueous composition does not comprise an agrochemical active ingredient.

* * * * *